US00PP15038P3

(12) United States Plant Patent
LaBonte et al.

(10) Patent No.: US PP15,038 P2
(45) Date of Patent: Jul. 27, 2004

(54) SWEETPOTATO PLANT NAMED 'L96-117'

(50) Latin Name: *Ipomoea batatas*
Varietal Denomination: L96-117

(75) Inventors: Don R. LaBonte, Baton Rouge, LA (US); Christopher A. Clark, Baton Rouge, LA (US); James M. Cannon, Baton Rouge, LA (US); Paul W. Wilson, Gonzales, LA (US); Arthur A. Villordon, Monroe, LA (US)

(73) Assignee: Board of Supervisors of Louisiana State University and Agricultural and Mechanical College, Baton Rouge, LA (US)

( * ) Notice: Subject to any disclaimer, the term of this patent is extended or adjusted under 35 U.S.C. 154(b) by 0 days.

(21) Appl. No.: 10/091,255

(22) Filed: Mar. 5, 2002

(65) Prior Publication Data

US 2003/0172423 P1 Sep. 11, 2003

(51) Int. Cl.[7] ..... A01H 5/00

(52) U.S. Cl. ..... Plt./258

(58) Field of Search ..... Plt./258

*Primary Examiner*—Kent Bell
(74) *Attorney, Agent, or Firm*—André J. Porter; John H. Runnels; Bonnie J. Davis

(57) ABSTRACT

A new variety of sweetpotato identified as 'L96-117' is disclosed having superior processing qualities and a high total-sugar content. 'L96-117' is characterized by an intense orange flesh and an elongated root.

3 Drawing Sheets

This invention pertains to a new and distinct variety of sweet potato.

SUMMARY OF THE INVENTION

Genus and species name: This new and distinct sweetpotato variety, *Ipomoea batatas* (L.) Lam., demonstrates both superior processing qualities and high total-sugar content as compared to other available sweetpotato varieties known to the inventors.

Variety denomination: This new and distinct sweetpotato variety is identified as 'L96-117', and is characterized by its dark orange flesh and its elongated roots.

BACKGROUND OF THE INVENTION

Sweetpotatoes, unlike Irish potatoes (*Solanum tuberosum*), are not tuber propagated plants. A "tuber" is a short, thickened portion of an underground branch. Along a tuber are found "eyes," each of which comprises a ridge bearing a scale-like leaf (analogous to a branch leaf) having minute meristematic buds in the axial of the leaf. By contrast, sweet potato roots are developmentally and anatomically true roots, lacking meristematic buds, and are not derived from an underground branch. Sweet potatoes do not form tubers.

BRIEF DESCRIPTION OF THE DRAWING

The file of this patent contains at least one photograph executed in color. Copies of this patent or patent application publication with color drawing(s) will be provided by the Office upon request and payment of the necessary fee.

DETAILED BOTANICAL DESCRIPTION

This new variety of sweetpotato, identified as 'L96-117', resulted from an open pollinated cross to the Louisiana Agricultural Experiment Station female parent 'L91-189' (unpatented) which was performed in 1995. The male parent is unkown. No patented male parents were among potential pollen sources in the crossing nursery. 'L96-117' was developed by the Louisiana Agricultural Experiment Station in Baton Rouge, La., to provide a variety with characteristics similar to 'Beauregard' (unpatented), but with improved processing qualities. The female parent 'L91-189' (unpatented) had similar disease resistance. 'L91-189' was discarded as a parent and no longer exists because of poor root shape; hence no comparison is given.

Color terminology used herein is in accordance with the MUNSELL® color charts for plant tissue and the MUNSELL® Book of Color for root skin and flesh determination (Munsell Color, GretagMacbeth LLC, New Windsor, N.Y.). The color descriptions and color illustrations are as nearly true as is reasonably possible. However, it is understood that both color and other phenotypic expressions described herein may vary from plant to plant with differences in growth, environment and cultural conditions, without any change in the genotype of the variety 'L96-117'.

'L96-117' roots were stored during the winter at the Louisiana Agricultural Experiment Station (Sweetpotato Research Station) in Chase, La. During the following spring 'L96-117' was planted and produced approximately 8–10 sprouts, which were cut and transplanted successfully for asexual reproduction. Asexual propagation of the new cultivar by cuttings at the Louisiana Agricultural Experiment Station has shown that the unique features of this new sweetpotato are stable and the plant reproduces true to type in successive generations of asexual propagation. Plants described herein are approximately 90–110 days in age from planting in full sun field plantings.

Figure 1:
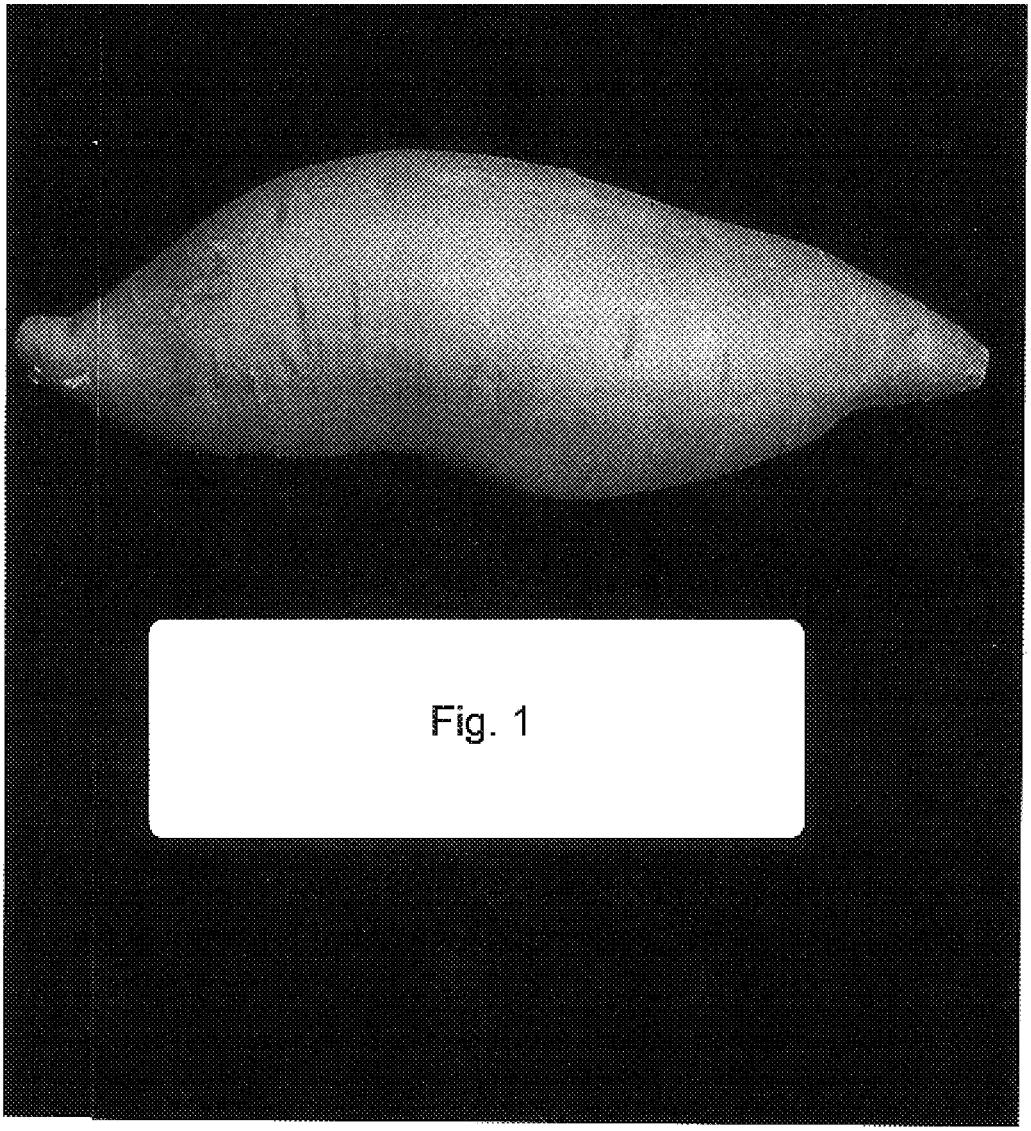
FIG. 1 is a color photograph of the growth form of the novel variety of sweet potato identified as 'L96-117'.
Figure 2:
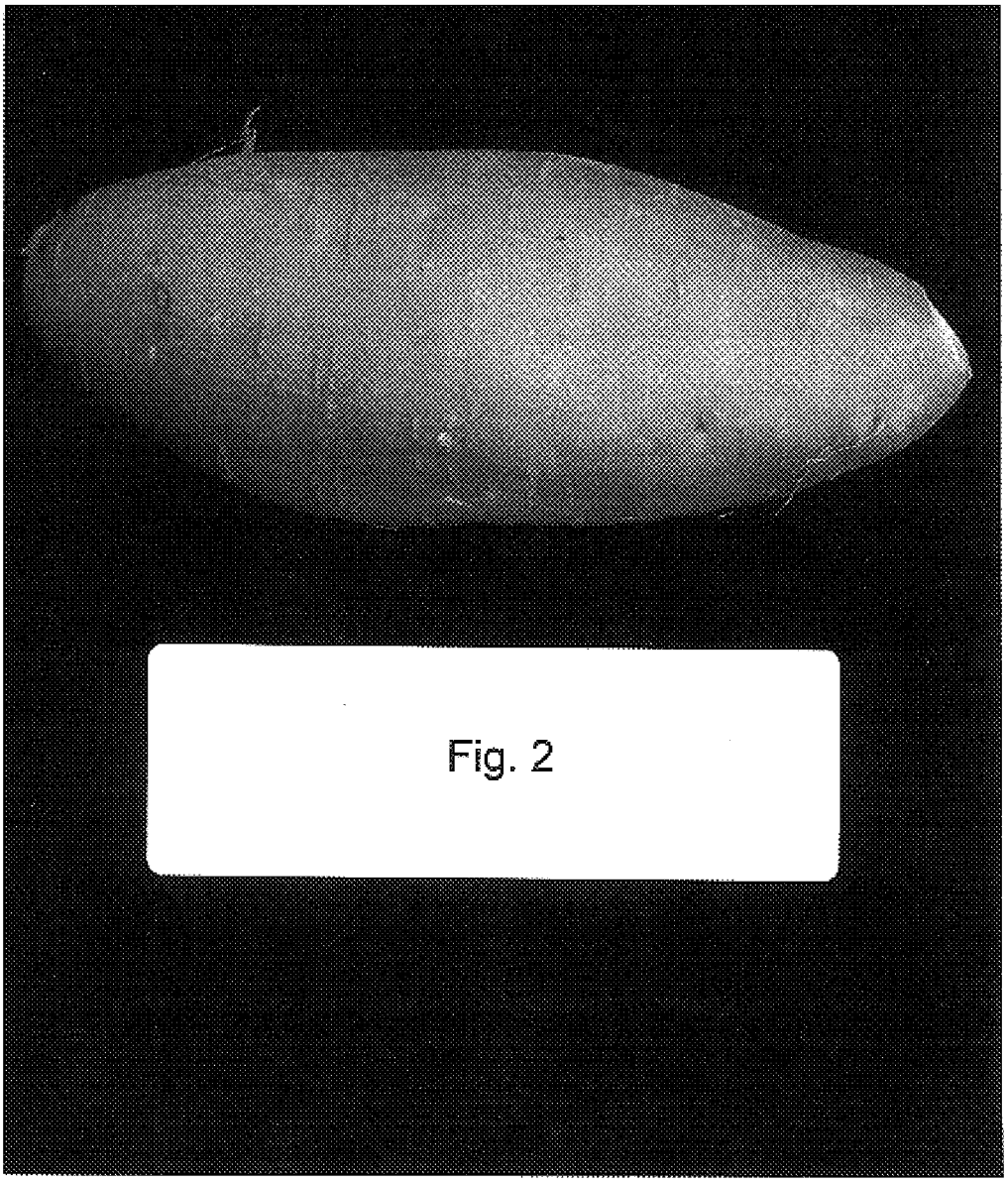
FIG. 2 is a color photograph of the growth form of the sweet potato variety identified as 'Beauregard'.

FIG. 1 depicts the fleshy root form of the 'L96-117' sweetpotato. Skin varies in color from light to dark rose, and is typically darker than 'Beauregard' at harvest (skin color lightens in storage). See 'Beauregard' as depicted in FIG. 2. Skin is smooth, similar to that of 'Beauregard'; however, the flesh is more uniformly orange than 'Beauregard', as depicted in FIG. 2. The cortex is 3–4 mm in depth. Colorimetric evaluations using the aforementioned color charts of skin and flesh for both 'L96-117' and 'Beauregard' storage roots at harvest, are shown in Table 1.

TABLE 1

| | Variety | Color[z] |
|---|---|---|
| Skin | 'L96-117' | 5 R (red)(4/6) |
| | 'Beauregard' | 7.5 R (red)(5/6) |
| Cortex | 'L96-117' | 2.5 Y (yellow) R (red)(7/12) |
| | 'Beauregard' | 5 Y (yellow) R (red)(8/6) |
| Flesh | 'L96-117' | 2.5 Y (yellow) R (red)(7/12) |
| | 'Beauregard' | 2.5 Y (yellow) R (red)(7/10) |

[z]Data represent color scale value using the MUNSELL ® Book of Color, color-order system.

Figure 3:
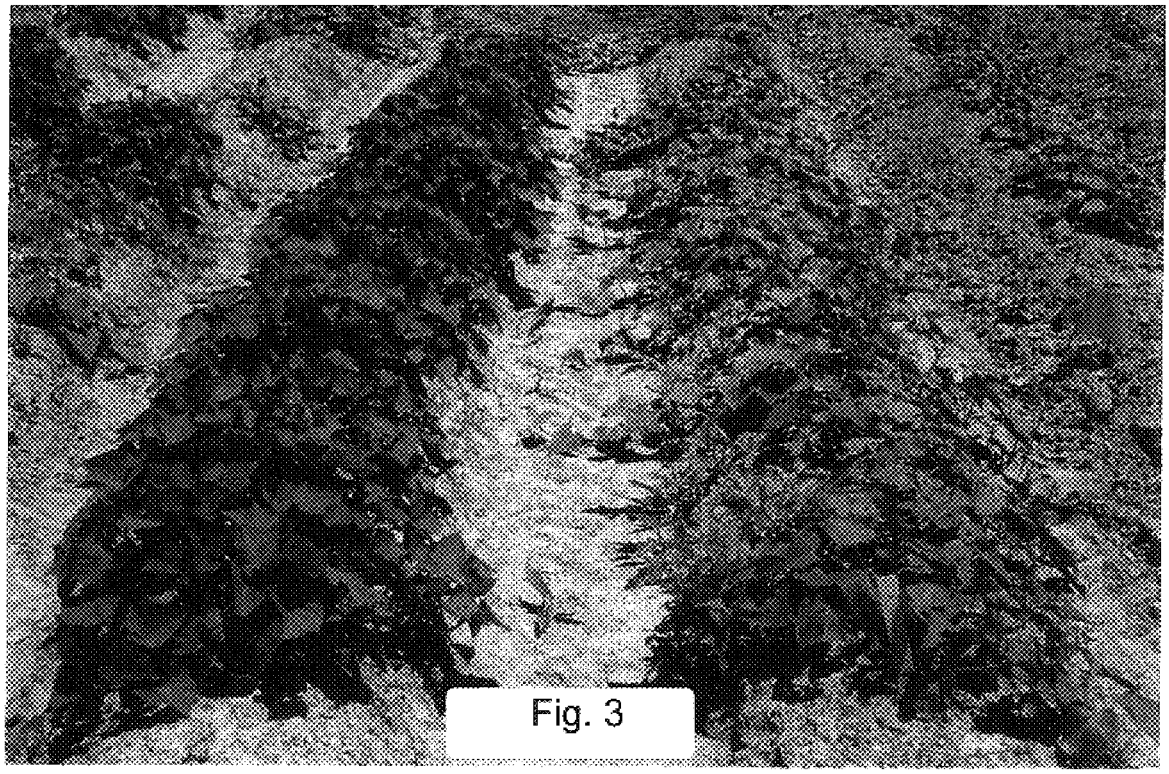
FIG. 3 is a color photograph of the canopy biomass of the novel variety of sweetpotato identified as 'L96-117'.

FIG. 3 depicts the canopy biomass of the 'L96-117' sweetpotato. 'L96-117' has green-stemmed vines [5 G (green) Y (yellow) (4/6)] from the apex to about 25 cm from the apex. The vines gradually change to a green with a purple cast [2.5 Y (yellow) R (red) (4/6)] at the crown of the roots. The appearance of the canopy biomass is greater than 'Beauregard' and less than another variety know as 'Jewel' (unpatented; not shown). See FIG. 2. The canopy architecture is prostrate (28–30 cm in height from the soil surface) and spreads to a radius of 45 cm, similar to 'Beauregard'. Between 3 to 4 main vines arise from the main stem near the soil surface. The main stem has a 1.5–2.0 cm diameter. The main vines have a length of 72–140 cm, a diameter of 0.4 cm at a distance of 65 cm from the base, a diameter of 1.0 cm at the base, and a diameter of 0.3 cm at the first internode of the first fully developed leaf from the apex. Between 2 to 5 lateral branches arise from each of the main vines. The length of the first internode beginning at the apex between the first and the second fully developed leaf is 7 cm. The internode length for other sections of the vine average between 6 to 7 cm. The upper and the lower surfaces of the unfolded immature leaves are dark green [5 G (green) Y (yellow) (4/6)]. The upper surface color gradually changes (over one to two nodes from the apex) to a darker green [5 G (green) Y (yellow) (3/4)], while the lower surface remains unchanged. The leaf margins from the edge to about 1–1.5 mm are purple [5 R (red) P (purple) (3/6)]. Mature leaves which are located five to six nodes away from the apex have an acute apex, a cordate base, and a smooth leaf margin. Each leaf has two moderate lobes in addition to the main lobe. Mature leaves have a length of 5.0 cm and a width of 7.0 cm. The abaxial veins are indistinguishable from the leaf in color [5 G (green) Y (yellow) (3/4)]. The adaxial veins are dark purple [5R (red) P (purple) (3/8)]. The petiole changes from purple [5 R (red) P (purple) (3/4)] near the leaf junction to green [7.5 G (green) Y (yellow) (4/4)] near the node. The petiole has a length of approximately 5 to 6 cm at a distance of five nodes from the apex, and has a diameter of 2–3 mm at a distance of 4 cm from the leaf junction. The dormant nodal meristem is also purple [5 R (red) P (purple) (4/6)].

A typical inflorescence of 'L96-117' has 7–8 flowers per peduncle. The peduncle is green [7.5 G (green) Y (yellow) (5/6)], and has a length of approximately 6 to 7 cm and a diameter of 2 mm. The flower bud (one day before opening) has a length of approximately 3 to 3.5 cm from the base of the calyx (calyx is 0.5 cm wide) to the tip of the closed corolla, and a maximum width of 0.5 cm. Bud shape is fusiform. The closed corolla is a purple [5 R (red) P (purple) (5/6)]. Sepal color and size are similar to an opened flower (described in more detail below). The individual opened flowers have a length of 4 to 5 cm from the base of the calyx. The five fused flower petals have a pentagonal pattern with a smooth edge and the corolla is 4 cm wide. The inner throat of the corolla is purple [5 R (red) P (purple) (5/8)], but changes to a lighter purple [5 R (red) P (purple) (8/4)] at the outer surface. The inner and outer limb of the corolla (corolla's outermost area, distal from the calyx) is a light purple [5 R (red) P (purple) (8/4)]. The five sepals, which form the calyx, are green [7.5 G (green) Y (yellow) (5/6)] (inner and outer surface), and have an elliptic shape with a cordate apex. The length and width of the sepal are 7 mm and 4 mm, respectively. The sepal margins are smooth. The stigma is white ([Munsell Grays R (red) Y (yellow) (9/10)] and has a length of 1.5 cm. Five stamens are attached to the ovary and are inferior to the stigma. No fragrance is present.

EXAMPLE 1

Tests Conducted

To confirm that 'L96-117' was a new variety, controlled tests (e.g., pathogen responses and yield) were conducted at the Louisiana Agricultural Experiment Station in Baton Rouge, La. 'Beauregard' was selected for comparison tests with 'L96-117' because of its commercial dominance in the U.S. sweetpotato acreage. 'Beauregard' occupies more than 70% of acreage devoted to sweetpotato in the U.S. Diseases that commonly affect the growth of sweet potatoes were selected to test for pathogen responses in both varieties. Scions of 'L96-117' and 'Beauregard' reacted similarly to most diseases evaluated in the controlled tests. 'L96-117' was less resistant to fusarium wilt, caused by *Fusarium axysporum* Schlect. f. sp. *batatas* (Wollenw.) Synd. & Hans., than was 'Beauregard'. However, 'L96-117' exhibited higher resistance to soil rot, caused by *Streptomyces ipomoeae* (Person and Martin) Waksman & Henrici., than did 'Beauregard'.

Nematode reproduction was measured in greenhouse tests. 'L96-117' exhibited higher resistance to the southern root-knot nematode, *Meloidogyme incognita* (Kofoid and White, 1919) Chitwood, 1949, race—3, than 'Beauregard'. Both 'L96-117' and 'Beauregard' were susceptible to the reniform nematode, *Rotylenchulus reniformis* Linford & Oliveria, 1940, 'L96-117' and 'Beauregard' were both resistant to the development of internal cork, a disease presumably caused by a virus (unknown). 'L96-117' and 'Beauregard' exhibited similar resistance to fusarium root rot caused by *Fusarium solani* (Mart.) Sacc. Emend. Snyd. & Hans. 'L96-117' exhibited higher resistance to bacterial root rot, caused by *Erwinia chrysanthemi* Burkholder, McFadden and Dimock, 1953, than did 'Beauregard'. 'L96-117' exhibited lower resistance to *Rhizopus stolonifer* (Her. Ex. Fr.) Lind., than did 'Beauregard'. Circular spot, caused by *Sclerotium rolfsii* Sacc., varied from a low to a high incidence in both 'L96-117' and 'Beauregard'.

No formal trials have been conducted to date on 'L96-117' for insect pests. 'L96-117' does not appear to show any novel insect resistance. Both 'L96-117' and 'Beauregard' show similar levels of susceptibility to important insect pests, most notably the banded cucumber beetle, *Diabrotica balteata* LeConte, and white grub, *Phyllophaga ephilda* Say.

To determine yield production, complete-block trials using four replications of '96-117' and 'Beauregard' each were conducted at two different Louisiana Agricultural Experiment Station locations, Burden Research Plantation in Baton Rouge, La. and the Sweet Potato Research Station in Chase, La. Both 'L96-117' and 'Beauregard' were transplanted in randomized complete-block trials at 31, 36, and 41 cm spacings, in Loring silt loam soil at the Burden Research Plantation and Gilbert silt loam soil at the Sweet Potato Research Station. Each block/plot was fertilized with 250 pounds per acre of nitrogen, $P_2O_5$, and $K_2O$ (about 250 pounds per acre of 13% N, 13% $P_2O_5$, and 13% $K_2O$, 13—13—13 mixed fertilizer). 'L96-117' was compared to 'Beauregard' at early and middle transplanting dates at each location beginning in June. Average yields were measured for the following grades of roots: U.S. #1 (51–89 mm in diameter, 76–229 mm long); Canner (25–51 mm in diameter, 51–178 mm long); and Jumbo (larger than U.S. #1 in diameter, length or both, and without objectionable defects). A typical marketable root of 'L96-117' has a length of 130–140 mm, a diameter of 60–70 mm, and a shape that is mostly round-elliptic. The base or distal end of 'L96-117' tends to be more elongated, while the apex or proximal end is slightly rounder. U.S. #1 roots weigh between 200 to 240 g. In comparison, U.S. #1 roots of 'Beauregard' weigh between 250–300 g, are less elongate at 17 cm in length in comparison to 'L96-117' at 20 cm in length. Root widths for both are, 5–7 cm. The cortex of 'L96-117' is 0.4 cm versus 0.5 cm for 'Beauregard'.

Early transplanting date trials were conducted at the Burden Research Plantation. 'L96-117' and 'Beauregard' were transplanted on June 13 and harvested on October 11 (120 days after planting). Producers usually consider 110 to 125 days a typical development period between planting and harvesting. (Variability occurs due to weather conditions.) Average yields, measured at $Mg.ha^{-1}$, are shown in Table 2.

TABLE 2

| Selection (spacing, in cm) | US #1† | Canners† | Jumbos† | TMY† |
|---|---|---|---|---|
| 'L96-117' (41) | 22.8a | 5.5b | 1.2bc | 29.5ab |
| 'L96-117' (36) | 22.8a | 5.7ab | 2.8abc | 31.3a |
| 'L96-117' (31) | 21.9a | 5.8ab | 2.6bc | 30.2ab |
| 'Beauregard' (41) | 22.4a | 5.3b | 4.0ab | 31.7a |
| 'Beauregard' (36) | 22.8a | 6.4ab | 5.6a | 34.8a |
| 'Beauregard' (31) | 25.1a | 6.8ab | 4.2ab | 36.0a |
| Least Significant Difference LSD (P < 0.05) | 5.6 | 2.1 | 3.0 | 6.3 |

†Average yields of varieties followed by a common letter do not differ significantly (P < 0.05) according to Duncan's Multiple Range Test.
TMY‡ = total marketable yield Middle transplanting date trials were also conducted at the Burden Research Plantation. 'L96-117' and 'Beauregard' were transplanted on June 22 and harvested on October 27 (127 days after planting). Average yields ($Mg.ha^{-1}$) of 'L96-117' and 'Beauregard' are shown in Table 3.

TABLE 3

| Selection (Spacing, in cm) | US #1† | Canners† | Jumbos† | TMY† |
|---|---|---|---|---|
| 'L96-117' (41) | 13.4a | 3.4b | 1.7a | 18.5ab |
| 'L96-117' (36) | 11.4a | 5.8ab | 3.2a | 20.3ab |
| 'L96-117' (31) | 10.5a | 7.3ab | 2.7a | 20.6ab |
| 'Beauregard' (41) | 7.6a | 4.7ab | 4.6a | 16.9b |
| 'Beauregard' (36) | 14.2a | 3.3b | 4.1a | 21.6ab |
| 'Beauregard' (31) | 17.1a | 13.4a | 7.9a | 38.5a |
| Least Significant Difference LSD (P < 0.05) | 7.5 | 7.0 | 6.1 | 15.5 |

†Average yields of varieties followed by a common letter do not differ significantly (P < 0.05) according to Duncan's Multiple Range Test.
TMY = total marketable yield Early transplanting date trials were also conducted at the Sweet Potato Research Station. 'L96-117' was transplanted on June 1 and harvested on September 27 (118 days after planting). ('Beauregard' was not included in this transplanting trial.) Average yields ($Mg.ha^{-1}$) by grade are shown in Table 4.

TABLE 4

| Selection (Spacing, in cm) | US #1 | Canners | Jumbos | TMY‡ |
|---|---|---|---|---|
| 'L96-117' (21) | 30.3 | 11.5 | 4.4 | 41.9 |
| 'L96-117' (36) | 25.6 | 11.4 | 1.0 | 37.1 |
| 'L96-117' (41) | 25.2 | 10.7 | 0.8 | 36.0 |
| Least Significant Difference LSD (P < 0.05) | 7.8 | 4.1 | 5.4 | 7.5 |

TMY = total marketable yield

Middle transplanting date trials were also conducted at the Sweet Potato Research Station. 'L96-117' and 'Beauregard' were transplanted on July 12, and harvested on October 31 (111 days after planting) using 31, 36 and 41 cm spacing. Average yields ($Mg.ha^{-1}$) by grade are shown in Table 5.

TABLE 5

| Selection (Spacing, in cm) | US #1† | Canners† | Jumbos† | TMY† |
|---|---|---|---|---|
| 'L96-117' (41) | 4.5c | 9.1b | 1.0a | 13.6c |
| 'L96-117' (36) | 5.4bc | 11.7ab | 0.9a | 17.1bc |
| 'L96-117' (31) | 4.6c | 11.7ab | 2.4a | 16.2c |
| 'Beauregard' (41) | 10.1a | 12.1ab | 0.6a | 22.1a |
| 'Beauregard' (36) | 9.2ab | 11.5ab | 1.6a | 20.9ab |
| 'Beauregard' (31) | 9.2ab | 13.8a | 0.6a | 23.1a |
| Least Significant Difference LSD (P < 0.05) | 4.2 | 4.8 | 3.2 | 4.3 |

†Average yields of varieties followed by a common letter do not differ significantly (P < 0.05) according to Duncan's Multiple Range Test.
TMY = total marketable yield As shown in Tables 2–5, 'L96-117' produced yields comparable to 'Beauregard' at early transplanting dates (95% of 'Beauregard' for U.S. #1 grade; 91% of 'Beauregard' for total marketable yield). Spacing had no significant effect on yield. (At later planting dates, L96-117 had yields slightly less than those of 'Beauregard', but still competitive. Replicated plots on sweet potato production farms have not shown any predisposition of 'L96-117' to low yield characteristics in late plantings.)

'L96-117' was also compared to 'Beauregard' for physiological attributes. Using replicates of seven month stored sweet potato roots, it was determined that 'L96-117' has an Alcohol Insoluble Solid (AIS) content (i.e., starch) of 14.5% (fresh wt. basis). By comparison, 'Beauregard' has an AIS content of 11.4% (AIS content of freshly harvested roots for 'L96-117' (25.2%) was similar to that of 'Beauregard' (23.2%)). 'L96-117' had higher total sugars (6.7%, 10 g fresh wt. basis) as compared to that of 'Beauregard' (5.2%) for seven month stored sweet potato roots. Puree-processed, freshly harvested roots of 'L96-117' had higher total sugar content (84 mg/gm fresh wt. basis) than did a comparable sample of 'Beauregard' (37 mg/gm fresh wt. basis).

'L96-117' produces plants (sprouts) at an earliness and quantity similar to 'Beauregard'. Days to harvest (about 110–120 days) are similar to, and sometimes greater than, 'Beauregard'. The roots of 'L96-117' are more elongated than those of 'Beauregard'. Yield of total and number one grade roots is slightly less than that of 'Beauregard'. A primary use of 'L96-117' is as a processor variety. Root length of 'L96-117' makes it less desirable for the fresh sweet potato market. However, the high sugar content and intense orange flesh of 'L96-117' make it well suited for production of a superior puree for uses such as baby food puree.

We claim:

1. A new and distinct variety of *Ipomoea batatas* plant named 'L96-117', as described and illustrated.

* * * * *